United States Patent [19]
Huntley

[11] Patent Number: 5,642,543
[45] Date of Patent: Jul. 1, 1997

[54] ADJUSTABLE ERGONOMIC PILLOW

[76] Inventor: James Benjamin Huntley, P.O. Box 55287, Washington, D.C. 20040

[21] Appl. No.: 643,606

[22] Filed: May 6, 1996

[51] Int. Cl.$^6$ .................................................. A47G 9/02
[52] U.S. Cl. ........................ 5/640; 5/490; 5/638; 5/645
[58] Field of Search ............................. 5/636, 640, 638, 5/722, 723, 728, 657, 922, 737, 738, 490

[56] References Cited

U.S. PATENT DOCUMENTS

| | | | |
|---|---|---|---|
| 1,211,548 | 1/1917 | Courts | 5/738 X |
| 1,271,672 | 7/1918 | Crowley et al. | 5/722 |
| 2,154,910 | 4/1939 | Mgaril | 5/722 |
| 5,136,741 | 8/1992 | Balonick et al. | 5/723 X |
| 5,360,017 | 11/1994 | Austin | 5/640 X |
| 5,528,784 | 6/1996 | Painter | 5/640 |

Primary Examiner—Michael F. Trettel
Attorney, Agent, or Firm—Charles Mabmel-Stein

[57] ABSTRACT

An incrementally adjustable ergonomic pillow, of a fitted fabric or other type holder for already shaped foam, poly or other type inserts, placed inside of the pillow case and held there by way of Velcro strips, zippers or other restraint attachments was developed because of the needs of the various sizes of persons engaged in the sleep process, due to those horizontal variations and vertical differences between the shoulder of different sizes of persons engaged in the sleep process, due to those horizontal variations in vertical differences between the shoulders of different size persons and the need of individuals to have a horizontal alignment of the entire system (tip of vertebrae where they join the base of the skull, neck vertebrae of the back) while lying on the sides, back or stomach while resting or sleeping. It also tends to inhibit snoring when an obstructed passageway for air may be the cause. Orthopedic and therapeutic values are imputed.

8 Claims, 2 Drawing Sheets

ADJUSTABLE ERGONOMIC PILLOW

BACKGROUND OF THE INVENTION

This invention pertains to an adjustable ergonomic pillow, non therapeutic non orthopedic in nature. More particularly, this invention relates to a removable formed material for supporting removable or addable cushions of variable thicknesses which when so added to or removed will raise or lower the head on a pillow surface in order to keep the spine and neck in the same horizontal plane for comfort while sleeping or resting.

As is well known, persons who are uncomfortable tend to relax fitfully and seem to be tired upon awakening. Our aim is to build in our pillow several degrees of density which determine the softness or firmness by varying the several types of inserts after adjusting for neck height.

As is well known, persons afflicted by pain or aches in various parts of the body, such as back, neck, shoulders or spine discomfort which is usually transmitted through the nervous system. Very frequently, such persons seek relief by positioning the uncomfortable part of their body on a support, such as a pillow or other like props already available in the house. Furthermore, in an attempt to provide a support having improved characteristics, various types of specially designed pillows have been described in patent literature. Thus, U.S. Pat. No. 1,262,510 to Kelly discloses a pneumatic pillow having a ventilator within its casing. U.S. Pat. No. 2,521,780 to Dodd describes a pneumatic headrest or cushion especially useful to support the head and portions of the neck. U.S. Pat. No. 2,612,645 to Boland teaches an air cushion comprising a plurality of upstanding partitions. U.S. Pat. No. 2,896,277 to Reed describes a pillow having a cylindrical front core and a hexadral elongated rear core; U.S. Pat. No. 3,644,949 to Diamond discloses an air cushion containing several separately inflatable sections disposed one above the other; U.S. Pat. No. 4,528,705 depicts a composite made of a sheet, the opposite ends of which are glued together and comprising an inflatable bag disposed within a large spherical end thereof; and U.S. Pat. No. 4,582,589 to Helwig teaches an inflatable seat cushion having several communicating chambers separated by crosspieces provided with openings for passage of air.

While the above-mentioned patents disclose the general concept of air inflatable support pillows, the present invention provides a new approach to a structural form of a cover especially developed for use in conjunction with an ergonomic support cushion which offers certain advantages different from the prior art devices. Just as the lower extremity needs a shoe size and additionally a shoe width, so does the upper extremity, the head, neck and vertebrae need to mesh for comfort and continuity while they support the body adequately and properly while a person is sleeping or resting.

OBJECTS OF THE INVENTION

In view of the foregoing, it is the principal object of the present invention to provide an adjustable ergonomic case or pillow specifically adapted for enclosing resilient cushions which may be inserted or removed to accommodate the various size individuals.

It is another object of the invention to provide an adjustable structural design for use in combination with polyfoam or other non therapeutic non orthopedic cushions.

A further objective of the invention is to provide, by the nature of its construction a stress, pain or fatigue relieving design comprising a cover providing different sizes, (thicknesses) cushioning mediums and resiliency to accommodate the needs of different sizes of individuals.

These and other objects will become more fully apparent as the description in its preferred embodiment proceeds in the following specification taken in conjunction with the accompanying drawings.

BRIEF SUMMARY OF THE INVENTION

In accordance with the invention, there is provided a flexible and adjustable cover for ergonomic support cushions, comprising an adjustable headrest, an all around sidewall and a bottom support wall the same size as the top head rest and adjustable fastening means of Velcro or other type fastener or snaps after raising or lowering the headrest to the most comfortable size for an individual. The removable or insertable polyfoam or other type fill foam will fill the void of inserting or removing the cushions.

BRIEF DESCRIPTION OF THE DRAWINGS

In the accompanying drawings, wherein like references designate corresponding elements throughout the views thereof.

DETAILED DESCRIPTION OF THE PREFERRED EMBODIMENT

Figure 1:
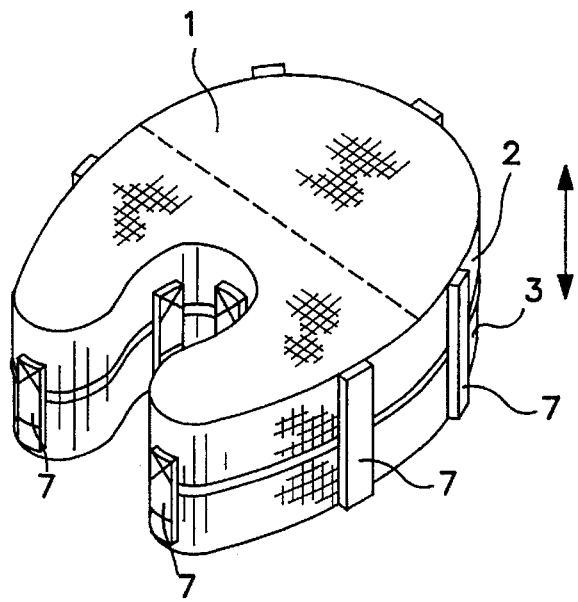
FIG. 1 is a perspective view of the case or headrest with inserts enclosed therein.
Figure 2:
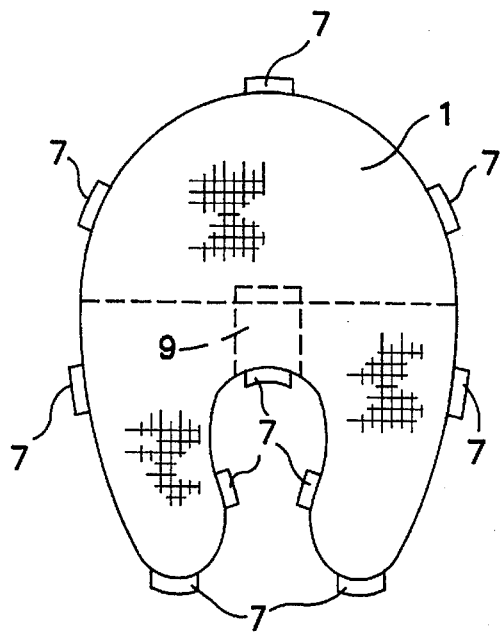
FIG. 2 is a plan view showing the shoulder support cut-out at the neck end of the pillow.
Figure 3:
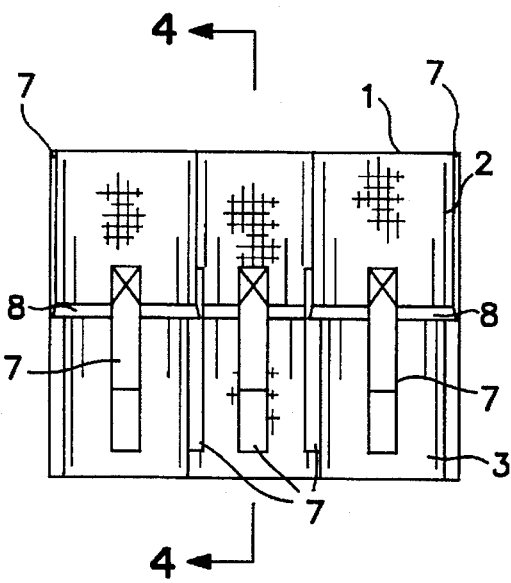
FIG. 3 is a view showing the Velcro or other fastening support mechanism.
Figure 4:
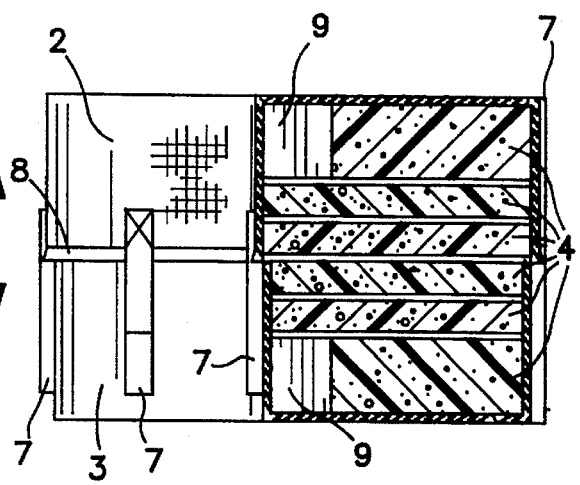
FIG. 4 shows the relative insert position within the case.
Figure 5:
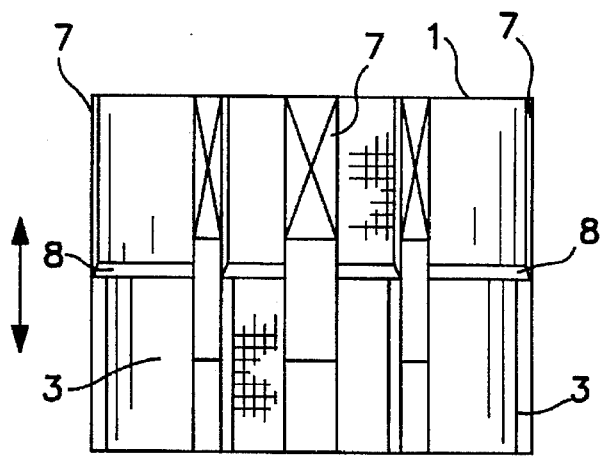
FIG. 5 shows the right side view and the rear connecting support of the top and bottom cases.
Figure 6:
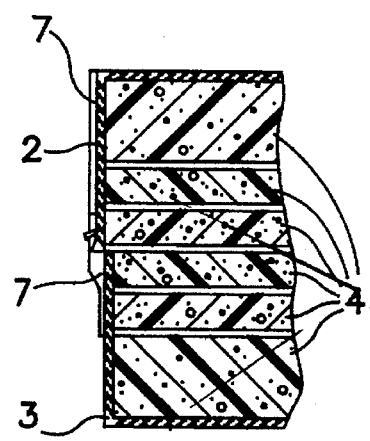
FIG. 6 shows a section blow-up of the removable, variable thickness and resiliency polyfoam or other type insert.
Figure 7:
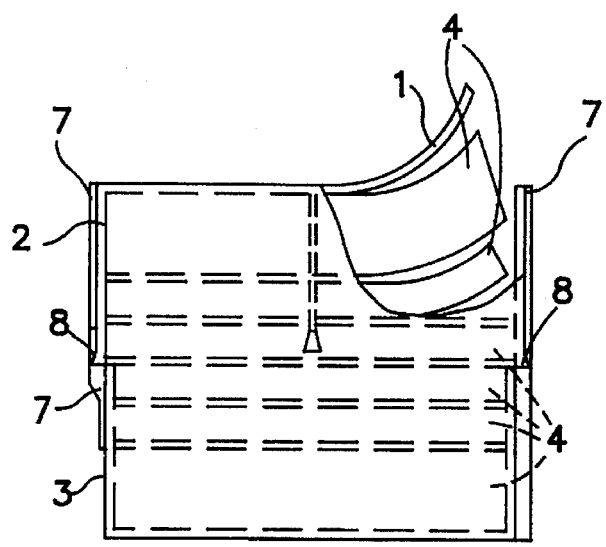
FIG. 7 shows the relationship between the inserts and the adjustable case.

It will be understood that various modifications in the form or in the construction details of our invention as herein described may be made without departing from the spirit thereof or the scope of the claims which follows:

Referring to the drawings, an adjustable, ergonomic pillow comprises two 2 and 3 adjustable casings, 2 being slidable downward over 3, so that the several removable, variable resiliency polyfoam or other type inserts 4 may be taken out of or added to the casings, as the case may be, to raise or lower the headrest 1, so that resiliency and height may be raised or lowered to accomodate the various sizes of individuals, as to their comfort zone or height, (distance from the tip of the shoulder up to the neck) where the vertebrae join the stem of the base of the skull, with all of these elements aligned horizontally so as to allow the maximum comfort for resting or sleeping.

Velcro tabs 7 facilitate the holding together of the components as they are changed in size to accommodate the various users. The flared bottom 8 of casing 2 helps facilitate the closing of casings 2 and 3 if an insert is removed or added to the pillow.

Part 9 denotes spaces for the ear.

I claim:

1. An adjustable pillow comprising:
    a top cover, having a top surface portion and a side portion, and a bottom cover having a bottom surface portion and a side portion, said side portion of said top cover fitting slidable over the said side portion of said bottom cover such that the top edge of the side portion of said bottom cover is covered by said side portion of said top cover, wherein said top cover can be raised or lowered with respect to said bottom cover to increase or decrease the space between said top surface portion of said top cover and said bottom surface portion of said bottom cover;

at least one compressible replaceable insert positioned between said top and bottom covers; and holding means attached to said side portions of said top and bottom covers for holding said top and bottom covers together such that the distance between said top, surface portion of said top cover and said bottom surface portion of said bottom cover is variable, wherein said holding means are releasable to provide access to the space between said top and bottom covers to permit the insertion or removal of said compressible inserts, whereby the number of inserts therebetween can be increased or decreased, thereby increasing or decreasing the height of the pillow.

2. An adjustable pillow, according to claim 1, wherein said top and bottom covers are substantially oval shaped, with a substantially "C" shaped inclusion at a narrow end of the oval for comfortably resting the head and neck of the user.

3. An adjustable pillow according to claim 1, wherein said inserts are comprised of foamed resilient material.

4. An adjustable pillow, according to claim 1, wherein said holding means comprises a plurality of releasable hook and loop fasteners attached across said top and bottom covers.

5. An adjustable pillow, according to claim 1, wherein at least one compressible replaceable insert is a plurality of compressible replaceable inserts.

6. An adjustable pillow, according to claim 5, wherein at least one of said plurality of compressible replaceable inserts has a resiliency which is greater than the resiliency of at least another one of said plurality of inserts.

7. An adjustable pillow, according to claim 5, wherein at least one of said plurality of compressible replaceable inserts has a thickness which is greater than the thickness of at least another one of said plurality of inserts.

8. An adjustable pillow comprising:

a top cover and a bottom cover, said top cover fitting slidably over said bottom cover wherein said top cover can be raised or lowered with respect to said bottom cover to increase or decrease the space between said top cover and said bottom cover, wherein said top and bottom covers are substantially oval shaped, with a substantially "C" shaped inclusion at a narrow end of the oval for comfortably resting the head and neck of the user;

a least one compressible replaceable insert positioned between said top and bottom covers; and holding means attached to said top and bottom covers for holding said top and bottom covers together, wherein said holding means are releasable to provide access to the space between said top and bottom covers to permit the insertion or removal of said compressible inserts, whereby the number of inserts therebetween can be increased or decreased, thereby increasing or decreasing the height of the pillow.

* * * * *